United States Patent
Klug et al.

(10) Patent No.: US 8,093,414 B2
(45) Date of Patent: Jan. 10, 2012

(54) PROCESS FOR PREPARING ACYLGLYCINATES BY MEANS OF DIRECT OXIDATION

(75) Inventors: Peter Klug, Grossostheim (DE); Achim Stankowiak, Altoetting (DE); Oliver Franke, Munich (DE); Franz-Xaver Scherl, Burgkirchen (DE); Ulf Pruesse, Braunschweig (DE); Nadine Decker, Braunschweig (DE); Klaus-Dieter Vorlop, Braunschweig (DE)

(73) Assignee: Clariant Finance (BVI) Limited, Tortola (VG)

( * ) Notice: Subject to any disclaimer, the term of this patent is extended or adjusted under 35 U.S.C. 154(b) by 373 days.

(21) Appl. No.: 12/377,835

(22) PCT Filed: Aug. 13, 2007

(86) PCT No.: PCT/EP2007/007128
§ 371 (c)(1),
(2), (4) Date: Mar. 24, 2009

(87) PCT Pub. No.: WO2008/019807
PCT Pub. Date: Feb. 21, 2008

(65) Prior Publication Data
US 2010/0286418 A1 Nov. 11, 2010

(30) Foreign Application Priority Data

Aug. 18, 2006 (DE) .......................... 10 2006 038 853

(51) Int. Cl.
*C07C 231/00* (2006.01)
(52) U.S. Cl. ....................................................... 554/63
(58) Field of Classification Search ....................... 554/63
See application file for complete search history.

(56) References Cited

U.S. PATENT DOCUMENTS

| | | |
|---|---|---|
| 6,703,517 B2 | 3/2004 | Hattori et al. |
| 6,828,452 B2 | 12/2004 | Raths et al. |
| 2005/0085651 A1 | 4/2005 | Kitamura et al. |
| 2010/0273879 A1 | 10/2010 | Klug et al. |
| 2010/0305358 A1 | 12/2010 | Klug et al. |

FOREIGN PATENT DOCUMENTS

| | | |
|---|---|---|
| EP | 1314717 | * 5/2003 |
| EP | 1672055 | 6/2006 |
| JP | 8053693 | 2/1996 |
| JP | 11 246473 | 9/1999 |
| WO | WO96/39375 | 12/1996 |
| WO | WO02/057217 | 7/2002 |
| WO | WO2008000648 | 1/2008 |
| WO | WO2008000671 | 1/2008 |

OTHER PUBLICATIONS

Choji Kashima et al: "Amino alcohols as C-terminal protecting groups in peptide synthesis" J. Chem Soc. Perkin Trans I, vol. 3 1988, pp. 535-539.*
International Search Report for PCT/EP2007/007128. 2, 2007.
Translation of International Preliminary Examination Report for PCT/EP2007/007128, 2007.
L. Prati, G. Martra, Gold Bull. 39 (1999) 96.
L. Prati, F. Porta, Applied catalysis A: General 291 (2005) 199-203.
S. Biella, G.L. Castiglioni, C. Fumagalli, L. Prati, M. Rossi, Catalysis Today 72 (2002) 43-49.
International Search Report for PCT/EP2008/009646, 2008.
Translation of International Preliminary Examination Report for PCT/EP2008/009646, 2008.
International Search Report for PCT/EP2009/000034, 2009.
Translation of International Preliminary Examination Report for PCT/EP2009/000034, 2009.
English Abstract for JP 11 246473, 1996.
English Abstract for JP 8053693, 1996.

* cited by examiner

*Primary Examiner* — Deborah D Carr
(74) *Attorney, Agent, or Firm* — Tod A. Waldrop

(57) ABSTRACT

A process is described for preparing acylglycinate salts of the formula (II) in which $R^1$ is a saturated linear or branched alkyl radical having from 1 to 21 carbon atoms or a mono- or polyunsaturated linear or branched alkenyl radical having from 2 to 21 carbon atoms, and B is a cation derived from a base, and/or the corresponding protonated acylglycines, characterized in that one or more fatty acid monoethanolamides of the formula (I) in which $R^1$ is as defined above is oxidized with oxygen in the presence of a transition group metal catalyst in an alkaline medium to give one or more acylglycinate salts of the formula (II), and, in the case of preparation of the protonated acylglycines, the acylglycinate salt(s) of the formula (II) is additionally reacted with an acid.

12 Claims, No Drawings

PROCESS FOR PREPARING ACYLGLYCINATES BY MEANS OF DIRECT OXIDATION

Amino acid surfactants are widespread in the laundry detergents industry and cosmetics industry. They belong to the group of mild cosurfactants and are usually used for improving the foam volume and the mildness of the formulations. They have in the past been synthesized mainly by reaction of amino acids with activated fatty acid derivatives, especially fatty acid chlorides, e.g. as described in U.S. Pat. No. 6,703,517 or US 2005/0085651 A1 for acylglycinates of the formula (IIa) (see scheme 1).

Scheme 1 Preparation of sodium acylglycinates according to the prior art.

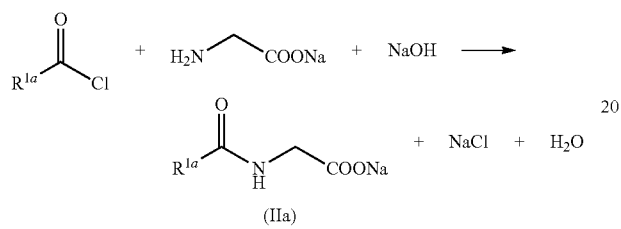

(IIa)

$R^{1a}$ is a saturated or unsaturated fatty acid radical having from 8 to 22 carbom atoms This process according to the prior art requires a relatively expensive and reactive raw material, namely the fatty acid chloride, and has the further disadvantage that one mole of sodium chloride NaCl is formed per mole of amino acid surfactant, i.e. the compound of the formula (IIa). This sodium chloride goes into the wastewater from the reaction and there represents a problem for biological water treatment plants since sodium chloride can impair the purification performance of such plants.

There is thus a need for a process for preparing amino acid surfactants, especially amino acid surfactants based on the amino acid glycine, known as acylglycinates and their protonated parent acids, which do not have the abovementioned disadvantages.

It has surprisingly been found that acylated glycines and salts thereof, known as acylglycinate salts or acylglycinates for short, can also be obtained, as an alternative to the customary fatty acid chloride route according to the prior art, by direct oxidation of fatty acid monoethanolamides by means of atmospheric oxygen or pure oxygen in the presence of transition metal catalysts.

The present invention accordingly provides a process for preparing acyl-glycinate salts of the formula (II)

(II)

where
$R^1$ is a saturated linear or branched alkyl radical having from 1 to 21 carbon atoms or a monounsaturated or polyunsaturated linear or branched alkenyl radical having from 2 to 21 carbon atoms and
B is a cation derived from a base,
and/or the corresponding protonated acylglycine acids, which comprises oxidizing one or more fatty acid monoethanolamides of the formula (I)

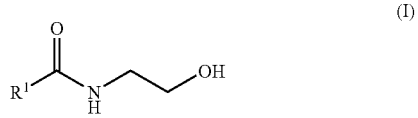

(I)

where $R^1$ is as defined above,
by means of oxygen in the presence of a transition metal catalyst in alkaline medium to form one or more acylglycinate salts of the formula (II) and, in the case of the preparation of the protonated acylglycine acids, additionally reacting the acylglycinate salt or salts of the formula (II) with an acid.

Compared to the use of the fatty acid chloride, the process of the invention starts out from a significantly cheaper raw material, viz. the fatty acid monoethanolamide of the formula (I). In addition, no salt is formed in the preparation of the acylglycinates of the formula (II) (see scheme 2).

Scheme 2
Preparation of acylglycinates and/or the corresponding protonated acylglycine acids by the process of the invention.

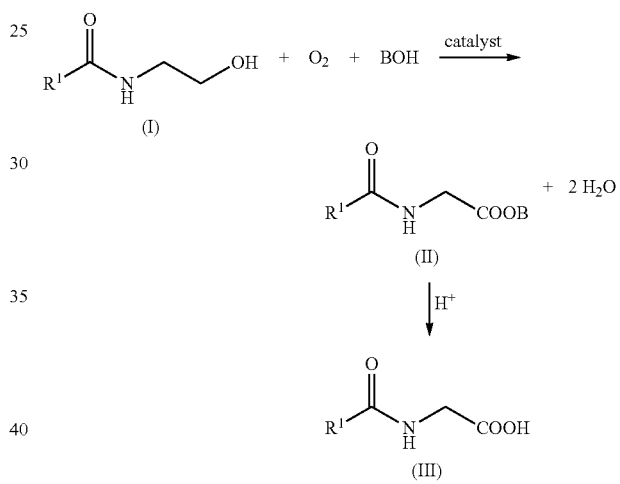

$R^1$ and B are as defined above

As fatty acid monoethanolamides, it is possible to use monoethanolamides of saturated, unbranched or branched fatty acids having 2-22 carbon atoms (i.e. $R^1 = C_1$-$C_{21}$) or of monounsaturated or polyunsaturated, unbranched or branched fatty acids having 3-22 carbon atoms (i.e. $R^1 = C_2$-$C_{21}$).

Preference is given to fatty acid monoethanolamides having 8-18 carbon atoms in the fatty acid radical or acyl radical $R^1CO$—, i.e. $R^1$ is in this case a saturated linear or branched alkyl radical having from 7 to 17 carbon atoms or a monounsaturated or polyunsaturated linear or branched alkenyl radical having from 7 to 17 carbon atoms. Particular preference is given to lauric acid monoethanolamide, myristic acid monoethanolamide, caprylic acid monoethanolamide, capric acid monoethanolamide, palmitic acid monoethanolamide, stearic acid monoethanolamide or isostearic acid monoethanolamide. Here, it is also possible to use amides based on chain fractions or mixtures of these fatty acid monoethanolamides, preferably coconut fatty acid monoethanolamide.

Among the saturated or unsaturated fatty acid monoethanolamides, preference is given to the saturated fatty acid monoethanolamides.

The counterion B is preferably an alkali metal cation selected from among cations of the alkali metals Li, Na, K, Rb and Cs. Particular preference is given to the cations of the alkali metals Na and K.

Preferred transition metal catalysts are heterogeneous noble metal catalysts. Suitable noble metals are copper, silver, gold, ruthenium, rhodium, palladium, osmium, iridium, platinum or mixtures thereof. Gold catalysts are preferred.

The transition metal catalyst is particularly preferably a nanogold catalyst. This means that the particle size of the gold particles is in the nanometer range.

The noble metals are preferably applied to supports. Preferred supports are activated carbon and oxidic supports, preferably titanium dioxide or aluminum oxide. Such catalysts can be produced as described in L. Prati, G. Martra, Gold Bull. 39 (1999) 96 and S. Biella, G. L. Castiglioni, C. Fumagalli, L. Prati, M. Rossi, Catalysis Today 72 (2002) 43-49 or L. Prati, F. Porta, Applied catalysis A: General 291 (2005) 199-203.

Particular preference is given to heterogeneous gold catalysts on a support, very particularly preferably those comprising nanosize gold. The nanogold catalyst is especially preferably applied to an oxidic support. This support preferably comprises titanium dioxide.

The nanogold catalysts preferably contain from 0.1 to 5% by weight of gold and particularly preferably from 0.5 to 2% by weight of gold.

The particle size of the gold particles of the nanogold catalysts is preferably 1-50 nm, particularly preferably 2-20 nm and very particularly preferably 4-10 nm.

As bases, it is possible to use carbonates, hydroxides or oxides in the process of the invention. Preference is given to the hydroxides BOH.

The process of the invention is preferably carried out in water.

The oxidation reaction is carried out at a temperature of from 10 to 80° C., preferably in the range from 30 to 70° C., particularly preferably in the range from 40 to 65° C.

The pH in the oxidation is preferably in the range from 8 to 13, particularly preferably in the range from 9 to 12.5.

The pressure in the oxidation reaction is preferably increased above atmospheric pressure.

The reaction in the alkaline medium firstly forms the alkali metal salts (B=Li, Na, K, Rb, Cs) of the acylated glycines having from 2 to 22 carbon atoms in the acyl radical, preferably 8 to 18 carbon atoms, preferably the sodium or potassium salts. The process is particularly preferably used for sodium cocoylglycinate and potassium cocoylglycinate. The acylated glycine can then be obtained from the solutions by acidification with inorganic acids. Preferred acids are hydrochloric acid and sulfuric acid.

In a further embodiment of the invention, account is taken of the fact that relatively long-chain ($\geq C_8$) fatty acid monoethanolamides, i.e. fatty acid monoethanolamides having 8 or more carbon atoms in the acyl radical $R^1CO$—, especially lauric acid monoethanolamide and coconut fatty acid monoethanolamide, are not sufficiently soluble in the reaction medium water for a satisfactory oxidation reaction without addition of suitable solvents. The advantage of the NaCl-free production of the target substances would in this case be partly lost again due to the additional use of solvents.

It has now been found that fatty acid monoethanolamides having 8 or more carbon atoms in the acyl radical $R^1CO$—, especially lauric acid monoethanolamide and coconut fatty acid monoethanolamide, are soluble in solutions of alkali metal salts of the acylglycinates or fatty acid glycinates, in particular the alkali metal salts of lauric acid glycinates or coconut fatty acid glycinates. This results in an elegant, solvent-free process comprising preparing a solution of fatty acid monoethanolamide in the target product acylglycinate salt, preferably sodium acylglycinate (this can be carried out by backmixing of the finished reaction solution with fatty acid monoethanolamide) and subjecting this mixture to the catalytic oxidation. The monoethanolamide present is thus oxidized and a solution of an alkali metal salt (B=Li, Na, K, Rb, Cs) of the acylglycine acid of the formula (III) in water is produced. Particular preference is given here to the sodium and potassium salts (B=Na, K).

The acylglycine acid of the formula (III) can subsequently be liberated from the alkaline reaction solution by means of suitable acids. Preferred acids are hydrochloric acid and sulfuric acid.

In a preferred embodiment of the invention, a solution comprising one or more fatty acid monoethanolamides of the formula (I) and one or more acylglycinates of the formula (II) is therefore subjected to oxidation.

In this preferred embodiment of the invention, the fatty acid monoethanolamides are oxidized by means of oxygen and heterogeneous transition metal catalysts, preferably heterogeneous gold catalysts, in alkali medium to form solutions of acylglycinates, with a solution of the fatty acid monoethanolamide in an alkali metal salt of an acylglycinate being present before commencement of the oxidation reaction and this mixture being subjected to the oxidation reaction in water.

In this preferred embodiment of the invention, the mass ratio of fatty acid monoethanolamide of the formula (I) to acylglycinate of the formula (II) at the beginning of the reaction is in the range from 1:10 to 3:1, preferably in the range from 1:2 to 2:1. The total proportion by mass of fatty acid monoethanolamide of the formula (I) and acylglycinate of the formula (II) is in the range from 15 to 50%, preferably in the range from 20 to 40%, particularly preferably in the range from 25 to 35%.

The process of the invention preferably gives solutions of acylglycinates of the formula (II) having only small residual contents of fatty acid monoethanolamide of <10% by weight, preferably <5% by weight, particularly preferably <2% by weight.

The following examples illustrate the invention:

EXAMPLE 1

Process for Preparing Glycinates Using Gold Catalysts 1 liter of an aqueous solution containing 15% by weight of coconut fatty acid monoethanolamide and 15% by weight of sodium cocoylglycinate is placed in a 2 liter pressure autoclave provided with sparging stirrer. This mixture is clear and liquid to 80° C. The amount of sodium cocoylglycinate can be taken from a previous batch or remain in the reactor from a previous oxidation batch. After addition of 5 g of a nanogold catalyst (1% by weight of gold on titanium dioxide, particle size: 4-8 nm), the suspension is brought to a pH of 12 by means of sodium hydroxide and heated to 60° C. After the reaction temperature has been reached, the reaction solution is pressurized with oxygen to a pressure of 9 bar and maintained at this pressure by introduction of further amounts. The pH of the mixture is maintained at 12 over the entire reaction time by means of sodium hydroxide introduced by means of an automatic titrator. After 10 hours, the reactor is cooled, vented and the catalyst is separated off from the reactor solution by filtration. The solution has a residual content of <2% by weight of coconut monoethanolamide and about 32% by weight of sodium cocoylglycinate.

EXAMPLE 2

Process for Preparing Glycinates Using Gold Catalysts 1 liter of an aqueous solution containing 15% by weight of coconut fatty acid monoethanolamide and 15% by weight of potassium cocoylglycinate is placed in a 2 liter pressure autoclave provided with sparging stirrer. This mixture is clear and liquid to 80° C. The amount of potassium cocoylglycinate can be taken from a previous batch or remain in the reactor from a previous oxidation batch. After addition of 5 g of a nanogold catalyst (1% by weight of gold on titanium dioxide, particle size: 4-8 nm), the suspension is brought to a pH of 12 by means of sodium hydroxide and heated to 60° C. After the reaction temperature has been reached, the reaction solution is pressurized with oxygen to a pressure of 9 bar and maintained at this pressure by introduction of further amounts. The pH of the mixture is maintained at 12 over the entire reaction time by means of potassium hydroxide introduced by means of an automatic titrator. After 10 hours, the reactor is cooled, vented and the catalyst is separated off from the reaction solution by filtration. The solution has a residual content of <1% by weight of coconut monoethanolamide and about 33% by weight of potassium cocoylglycinate.

The invention claimed is:

1. A process for preparing a acylglycinate salt of the formula (II)

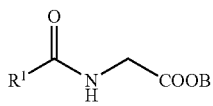

(II)

wherein
R$^1$ is a saturated linear or branched alkyl radical having from 1 to 21 carbon atoms, or a monounsaturated or polyunsaturated linear or branched alkenyl radical having from 2 to 21 carbon atoms and
B is a cation derived from a base,
and/or the corresponding protonated acylglycine acid, which comprises oxidizing at least one fatty acid monoethanolamide of the formula (I)

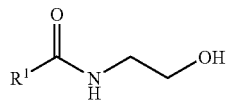

(I)

wherein R$^1$ is as defined above,
with oxygen in the presence of a transition metal catalyst in alkaline medium to form at least one acylglycinate salt of the formula (II) and, in the case of the preparation of the protonated acylglycine acid, additionally reacting the acylglycinate salt or salts of the formula (II) with an acid.

2. The process as claimed in claim 1, wherein at least one fatty acid monoethanolamide of the formula (I), wherein radical R$^1$ is a saturated linear or branched alkyl radical having from 7 to 17 carbon atoms, or a monounsaturated or polyunsaturated linear or branched alkenyl radical having from 7 to 17 carbon atoms, is used in the reaction.

3. The process as claimed in claim 1, wherein the at least one fatty acid monoethanolamide of the formula (I) is selected from the group consisting of: lauric acid monoethanolamide, myristic acid monoethanolamide, caprylic acid monoethanolamide, capric acid monoethanolamide, palmitic acid monoethanolamide, stearic acid monoethanolamide, isostearic acid monoethanolamide and coconut fatty acid monoethanolamide.

4. The process as claimed in claim 1, wherein the transition metal catalyst is selected from the group consisting of: a Cu catalyst, a Ag catalyst, a Au catalyst, a Ru catalyst, a Rh catalyst, a Pd catalyst, a Os catalyst, a Ir catalyst, a Pt catalyst and a mixture thereof.

5. The process as claimed in claim 1, wherein the transition metal catalyst is a gold catalyst.

6. The process as claimed in claim 5, wherein the transition metal catalyst is a nanogold catalyst.

7. The process as claimed in claim 6, wherein the nanogold catalyst has been applied to an oxidic support.

8. The process as claimed in claim 7, wherein the oxidic support comprises titanium dioxide.

9. The process as claimed in claim 6, wherein the nanogold catalyst contains from 0.1 to 5% by weight of gold.

10. The process as claimed in claim 6, wherein the particle size of the gold particles of the nanogold catalyst is from 1 to 50 nm.

11. The process as claimed in claim 1, wherein a solution comprising at least one fatty acid monoethanolamide of the formula (I) and at least one acylglycinate of the formula (II) is subjected to the oxidation.

12. The process as claimed in claim 6, wherein the nanogold catalyst contains from 0.5 to 2% by weight of gold.

* * * * *